(12) United States Patent
Endo (10) Patent No.: US 11,862,327 B2
(45) Date of Patent: Jan. 2, 2024

(54) MEDICAL IMAGE PROCESSING SYSTEM (71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 17/169,515

(22) Filed: Feb. 7, 2021

(65) Prior Publication Data

US 2021/0158528 A1 May 27, 2021

Related U.S. Application Data

(63) Continuation of application No. PCT/JP2019/032274, filed on Aug. 19, 2019.

(30) Foreign Application Priority Data

Aug. 20, 2018 (JP) ................................ 2018-154121

(51) Int. Cl.
*G06K 9/00* (2022.01)
*G16H 30/40* (2018.01)
(Continued)

(52) U.S. Cl.
CPC ....... *G16H 30/40* (2018.01); *A61B 1/000094* (2022.02); *G06T 7/0016* (2013.01);
(Continued)

(58) Field of Classification Search
CPC .............................. G06T 7/0012–0016; G06T 2207/10064–10136; G06T 2207/30004–30104; G06T 2207/30096; G06T 2207/30032; G06T 2207/30064;
G06T 7/0014; G06T 7/11; G06T 11/206; G06T 11/203; G06T 11/20; G06T 11/001; G06T 11/00; G06T 11/60; G06T 19/20;
(Continued)

(56) References Cited

U.S. PATENT DOCUMENTS 9,483,114 B2 11/2016 Maeda
2009/0131746 A1 5/2009 Seo et al.
(Continued)

FOREIGN PATENT DOCUMENTS

CN 101005794 7/2007
CN 102740757 10/2012
(Continued)

OTHER PUBLICATIONS

"Search Report of Europe Counterpart Application", dated Sep. 9, 2021, p. 1-p. 9.
(Continued)

*Primary Examiner* — Atiba O Fitzpatrick
(74) *Attorney, Agent, or Firm* — JCIPRNET (57) ABSTRACT

A remaining time calculation unit calculates, based on a notification waiting time indicating a time from when a feature region is recognized to when a notification of a recognition result of the feature region is started and a count time counted by a time count unit, a remaining time until the notification of the recognition result of the feature region is provided. A display control unit displays on a monitor remaining time notification information obtained based on at least the remaining time.

12 Claims, 8 Drawing Sheets

(51) Int. Cl.
    *G06T 7/00* (2017.01)
    *A61B 1/00* (2006.01)
(52) U.S. Cl.
    CPC ............ *G06T 2207/10068* (2013.01); *G06T 2207/30028* (2013.01); *G06T 2207/30096* (2013.01)
(58) Field of Classification Search
    CPC ....... G06T 2219/004; G06T 2219/2012; G06T 2200/24; G06T 2210/12; G06T 2210/41; G06T 2207/10068; G06T 2207/30028; G06T 2207/30048; G06T 2207/30052; G06T 2207/30056; G06T 2207/30061; G06T 7/174; G06T 7/74; G06V 2201/03–034; G06V 2201/032; G06V 10/25; G06V 10/764; G06V 10/751; G06V 2201/031; G06V 10/759; G06V 30/19013; A61B 1/000094; A61B 5/7485; A61B 6/469; A61B 1/00045; A61B 1/00048; A61B 6/461; A61B 6/465; A61B 1/00055; A61B 1/00043; A61B 10/04; A61B 1/2676; A61B 1/00009; A61B 1/2736; A61B 1/041; G16H 30/40
    See application file for complete search history.

(56) References Cited

U.S. PATENT DOCUMENTS

| | | | |
|---|---|---|---|
| 2012/0274754 A1 | 11/2012 | Tsuruoka | |
| 2012/0321759 A1* | 12/2012 | Marinkovich | A61B 5/442 356/402 |
| 2013/0152020 A1* | 6/2013 | Nishiyama | G16H 30/20 715/835 |
| 2014/0254760 A1 | 9/2014 | Hiroike et al. | |
| 2015/0187063 A1 | 7/2015 | Takahashi | |
| 2017/0156689 A1 | 6/2017 | Shinotsuka et al. | |
| 2018/0242817 A1 | 8/2018 | Imaizumi et al. | |
| 2018/0249900 A1 | 9/2018 | Imaizumi et al. | |
| 2018/0255167 A1* | 9/2018 | Saito | G16H 30/40 |
| 2020/0350075 A1* | 11/2020 | Noch | G10L 25/66 |
| 2021/0042915 A1* | 2/2021 | Bernat | G06F 18/2413 |

FOREIGN PATENT DOCUMENTS

| | | |
|---|---|---|
| CN | 104640496 | 5/2015 |
| CN | 105873539 | 8/2016 |
| EP | 3360461 | 8/2018 |
| EP | 3831272 | 6/2021 |
| JP | 2007151594 | 6/2007 |
| JP | 2010233724 | 10/2010 |
| JP | 2011160848 | 8/2011 |
| JP | 2011255006 | 12/2011 |
| JP | 2014171523 | 9/2014 |
| JP | 2015112429 | 6/2015 |
| JP | 2017104200 | 6/2017 |
| WO | 2017073338 | 5/2017 |
| WO | 2017081976 | 5/2017 |

OTHER PUBLICATIONS

"International Search Report (Form PCT/ISA/210) of PCT/JP2019/032274," dated Nov. 12, 2019, with English translation thereof, pp. 1-5.

"Written Opinion of the International Searching Authority (Form PCT/ISA/237) of PCT/JP2019/032274," dated Nov. 12, 2019, with English translation thereof, pp. 1-10.

"Office Action of Japan Counterpart Application", dated May 17, 2022, with English translation thereof, p. 1-p. 8.

"Office Action of Japan Counterpart Application" with English translation thereof, dated Feb. 1, 2022, p. 1-p. 6.

"Office Action of China Counterpart Application", dated Aug. 26, 2023, with English translation thereof, p. 1-p. 16.

* cited by examiner

MEDICAL IMAGE PROCESSING SYSTEM

CROSS-REFERENCE TO RELATED APPLICATIONS

This application is a Continuation of PCT International Application No. PCT/JP2019/032274 filed on 19 Aug. 2019, which claims priority under 35 U.S.C § 119(a) to Japanese Patent Application No. 2018-154121 filed on 20 Aug. 2018. The above application is hereby expressly incorporated by reference, in its entirety, into the present application.

BACKGROUND OF THE INVENTION

1. Field of the Invention

The present invention relates to a medical image processing system using an analysis result of a medical image.

2. Description of the Related Art

In the current medical field, medical image processing systems using medical images, such as an endoscope system including a light source device, an endoscope, and a processor device, are widely used. In recent years, diagnostic information regarding the state of a disease has been acquired by recognizing a feature region containing a potential lesion portion from a medical image and performing image analysis on the recognized feature region.

For example, in WO2017/073338A (corresponding to US2018/0242817A1), a feature region in a medical image is detected based on a specific feature value for the medical image. In response to the detection of the feature region, a notification image notifying that the feature region has been detected is displayed in an outer screen, and the feature region is displayed in a highlighted manner in an inner screen at a timing different from the timing of providing a notification using the notification image. In WO2017/081976A (corresponding to US2018/0249900A1), when a feature region is detected, the feature region is not immediately displayed in a highlighted manner, but the feature region is displayed in a highlighted manner in an observation image input after the lapse of a predetermined time.

SUMMARY OF THE INVENTION

As described above, a feature region is recognized from a medical image, and the recognition result is provided to a user, thereby improving the accuracy of diagnosis made by the user. On the other hand, if a recognition result of the feature region based on the medical image is provided before the user finds the feature region and performs discrimination, the user's attention may be distracted.

To address this problem, delaying a notification of the recognition result of the feature region, such as, as in WO2017/081976A, displaying the feature region in a highlighted manner after the lapse of a predetermined time, can prevent the distraction of the user's attention. In this case, however, the user does not know whether recognition processing is being performed correctly or the recognition processing has failed in a period until the recognition result is displayed.

It is an object of the present invention to provide a medical image processing system in which when notification of a recognition result of a feature region is delayed, a user is able to grasp whether recognition processing is being performed correctly or the recognition processing has failed in a period until the recognition result is displayed.

A medical image processing system of the present invention includes a medical image acquisition unit, a feature region recognition unit, a time count unit, a remaining time calculation unit, and a display control unit. The medical image acquisition unit acquires a medical image obtained by imaging of an observation target. The feature region recognition unit recognizes a feature region in the medical image. The time count unit counts a time from a timing at which the feature region is recognized. The remaining time calculation unit calculates a remaining time until a notification of a recognition result of the feature region is provided, based on a notification waiting time and a count time counted by the time count unit, the notification waiting time indicating a time from when the feature region is recognized to when the notification of the recognition result of the feature region is started. The display control unit displays remaining time notification information on a display unit, the remaining time notification information being obtained based on at least the remaining time.

Preferably, the remaining time notification information is represented by a remaining time notification geometric shape representing the remaining time using a geometric shape, and the remaining time notification geometric shape changes in accordance with the remaining time. Preferably, the remaining time notification geometric shape is a time bar. Preferably, the remaining time notification information is a remaining time notification value representing the remaining time using a value. Preferably, the remaining time notification information is remaining time notification audio representing the remaining time using audio. Preferably, the remaining time notification information is a display style of the recognition result of the feature region that changes in accordance with the remaining time. Preferably, the display style of the recognition result is highlighting applied to the feature region.

Preferably, the recognition result includes a result of discrimination processing for discriminating the feature region. Preferably, the time count unit counts the time based on an imaging time related to imaging of the observation target. Preferably, the time count unit counts the time based on the number of acquired frames indicating the number of medical images that are acquired.

Preferably, the medical image processing system further includes an identical-region determination unit that determines, in a case where the feature region is recognized in a medical image at a first timing, whether a feature region that is identical to the feature region is also present in a medical image at an N-th timing different from the first timing, and the time count unit continues counting the time when it is determined that the identical feature region is present. Preferably, the display control unit displays the recognition result of the feature region on the display unit in response to the count time reaching the notification waiting time.

According to the present invention, when notification of a recognition result of a feature region is delayed, a user is able to grasp whether recognition processing is being performed correctly or the recognition processing has failed in a period until the recognition result is displayed.

BRIEF DESCRIPTION OF THE DRAWINGS

FIG. 1 is a block diagram illustrating an image processing system, an endoscope system, and so on;

DESCRIPTION OF THE PREFERRED EMBODIMENTS

Figure 1:
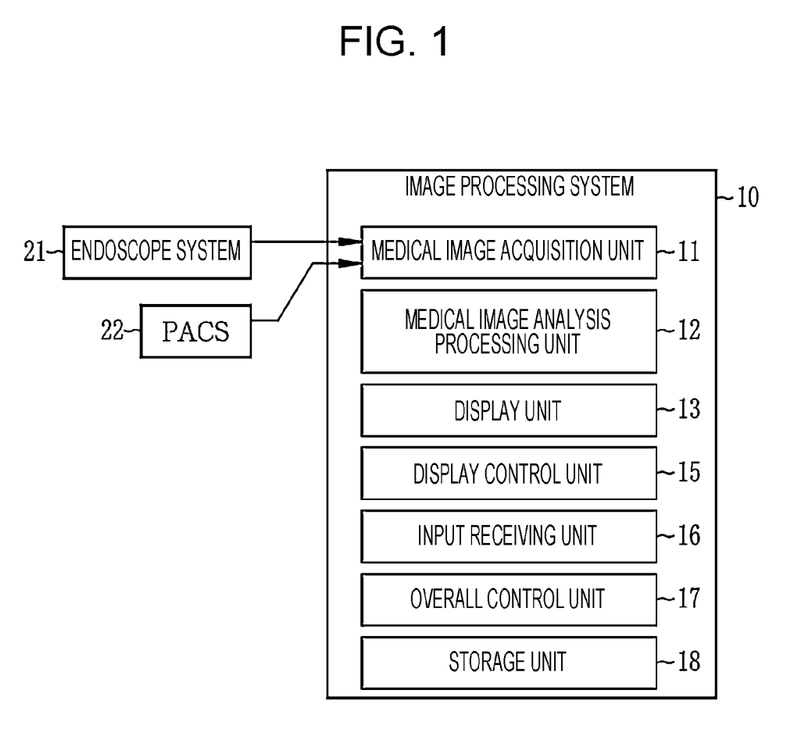

As illustrated in FIG. 1, an image processing system 10 includes a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a photographic subject image directly from an endoscope system 21 or the like that is a medical apparatus, or via a management system such as a PACS (Picture Archiving and Communication System) 22 or any other information system. The medical image is a still image or a moving image (so-called examination moving image). When the medical image is a moving image, the medical image acquisition unit 11 can acquire, as still images, frame images constituting the moving image after an examination. When the medical image is a moving image, furthermore, displaying the medical image includes displaying a still image of one representative frame constituting the moving image, and reproducing the moving image one or a plurality of times. The medical image acquired by the medical image acquisition unit 11 includes an image captured by a doctor using a medical apparatus such as the endoscope system 21, and an image automatically captured by the medical apparatus such as the endoscope system 21 regardless of an image-capturing instruction given by the doctor. In this embodiment, since the image processing system 10 and the endoscope system 21 perform image processing using a medical image, both the image processing system 10 and the endoscope system 21 correspond to a medical image processing system.

When a plurality of medical images can be acquired, the medical image acquisition unit 11 can selectively acquire one or a plurality of medical images among these medical images. Further, the medical image acquisition unit 11 can acquire a plurality of medical images acquired in a plurality of different examinations. For example, the medical image acquisition unit 11 can acquire either or both of a medical image acquired in an examination performed in the past and a medical image acquired in the latest examination. That is, the medical image acquisition unit 11 can arbitrarily acquire a medical image.

In this embodiment, a plurality of medical images including photographic subject images are acquired. More specifically, in a case where a medical image captured in a single specific examination is acquired and there is a plurality of medical images captured in a single specific examination, a plurality of medical images are acquired from among the series of medical images. In this embodiment, furthermore, the image processing system 10 is connected to the endoscope system 21 to acquire a medical image from the endoscope system 21. That is, in this embodiment, a medical image is an endoscopic image.

The display unit 13 is a display that displays the medical image acquired by the medical image acquisition unit 11 and an analysis result obtained by the medical image analysis processing unit 12. A monitor or display included in a device to which the image processing system 10 is connected can be shared and used as the display unit 13 of the image processing system 10. The display control unit 15 controls a display style of the medical image and the analysis result on the display unit 13.

The input receiving unit 16 accepts an input from a mouse, a keyboard, or any other operating device connected to the image processing system 10. The operation of the units of the image processing system 10 can be controlled using these operating devices.

The overall control unit 17 performs overall control of the operation of the units of the image processing system 10. When the input receiving unit 16 receives an operation input using an operating device, the overall control unit 17 controls the units of the image processing system 10 in accordance with the operation input.

The storage unit 18 stores a still image or the like of a medical image in a storage device (not illustrated) such as a memory included in the image processing system 10 or in a storage device (not illustrated) included in the medical apparatus such as the endoscope system 21 or the PACS 22.

Figure 2:
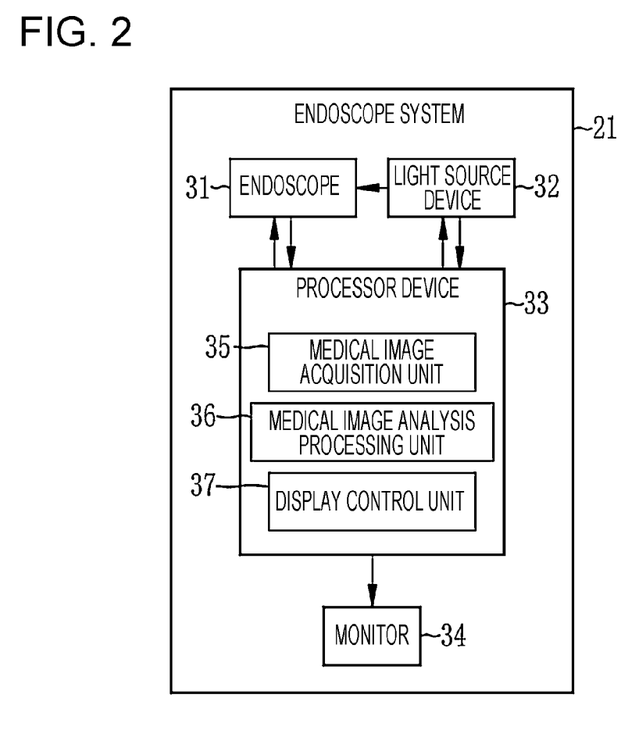
FIG. 2 is a block diagram illustrating the endoscope system.

As illustrated in FIG. 2, in this embodiment, the endoscope system 21 to which the image processing system 10 is connected includes an endoscope 31 that captures an image of a photographic subject irradiated with at least one of light in the white wavelength range or light in a specific wavelength range to acquire an image, a light source device 32 that irradiates the inside of the photographic subject with illumination light via the endoscope 31, a processor device 33, and a monitor 34 that displays a endoscopic image or the like captured using the endoscope 31. The light in the specific wavelength range to be used as illumination light by the endoscope 31 is, for example, light in a shorter wavelength range than the green wavelength range and is, in particular, light in the blue range or violet range in the visible range.

The processor device 33 includes a medical image acquisition unit 35, a medical image analysis processing unit 36, and a display control unit 37. The medical image acquisition unit 35 acquires the medical image output from the endoscope 31. The medical image analysis processing unit 36 performs analysis processing on the medical image acquired by the medical image acquisition unit 35. The content of the processing performed by the medical image analysis processing unit 36 is similar to the content of the processing performed by the medical image analysis processing unit 12 of the image processing system 10. The display control unit 37 displays the medical image obtained by the medical image analysis processing unit 36 on the monitor 34. The processor device 33 is connected to the image processing system 10. The medical image acquisition unit 35 is similar to the medical image acquisition unit 11, the medical image analysis processing unit 36 is similar to the medical image analysis processing unit 12, and the display control unit 37 is similar to the display control unit 15.

Figure 3:
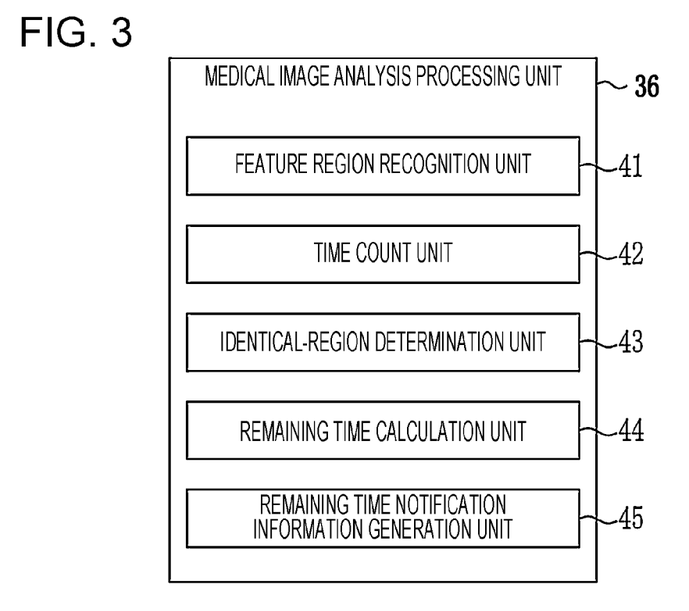
FIG. 3 is a block diagram illustrating the functions of a medical image analysis processing unit.

The medical image analysis processing unit 36 performs analysis processing using the medical image acquired by the medical image acquisition unit 35. As illustrated in FIG. 3, the medical image analysis processing unit 36 includes a feature region recognition unit 41, a time count unit 42, an identical-region determination unit 43, a remaining time calculation unit 44, and a remaining time notification information generation unit 45.

The feature region recognition unit 41 performs feature region recognition processing for recognizing a feature region from a medical image. The feature region recognition processing includes feature region detection processing for detecting a feature region from a medical image, and discrimination processing for discriminating the feature region. The result of the feature region detection processing and the result of the discrimination processing are displayed on the monitor 34 as the recognition result of the feature region after a notification waiting time has elapsed, as described below. As a method for providing a notification of the result of the feature region detection processing, a notification of the detection result may be provided by, for example, enclosing the feature region with a rectangular bounding box.

In the discrimination processing, the malignancy grade of an abnormality (hereinafter referred to as a lesion or the like) included in the feature region is discriminated. More specifically, the type of the lesion or the like or the stage of the lesion or the like is discriminated, and the malignancy grade is determined using the discriminated type or stage of the lesion or the like. The malignancy grade is an evaluation indicating importance in the diagnosis of a lesion or the like, and is an evaluation reflecting at least the type of the lesion or the like or the stage of the lesion or the like (when the "lesion or the like" is a treatment mark or the like, the progress status). The malignancy grade can be represented in a stepwise manner by, for example, "0" to "100", where "0" indicates benign, with the malignancy grade increasing as the number increases.

For example, in the discrimination processing, when the lesion or the like is a polyp, the type of the lesion or the like is discriminated as any one of hyperplastic polyp, SSA/P, adenoma, or cancer. When the lesion or the like is a cancer, the stage of the lesion or the like is discriminated by classification of endoscopic findings. For example, in the case of a large intestine tumor, examples of the classification of endoscopic findings include NICE (The Narrow-band imaging International Colorectal Endoscopic) classification, and JNET (The Japan NBI (Narrow Band Imaging) Expert Team) classification. Also when the lesion or the like is an inflammatory bowel disease, the stage of the lesion or the like is discriminated by classification of endoscopic findings. For example, for ulcerative colitis, which is one of inflammatory bowel diseases, examples of the classification of endoscopic findings include Mayo classification and Matts classification.

In the discrimination processing, one or a plurality of predetermined feature values are calculated, and the calculated feature value or values are used to discriminate the type or stage of the lesion or the like. In the discrimination processing, furthermore, the type or stage of the lesion or the like can be discriminated by, instead of using a feature value, texture analysis or pattern matching using a regular shape.

Examples of the feature region recognition processing include NN (Neural Network), CNN (Convolutional Neural Network), AdaBoost, and random forest. Alternatively, the feature region recognition processing may involve recognizing a feature region on the basis of a feature value obtained as color information of the medical image, the gradient of pixel values, or the like. The gradient of pixel values or the like changes according to, for example, the shape of the photographic subject (such as generalized ups and downs or localized depression or elevation in a mucous membrane), color (color such as from inflammation, bleeding, redness, or whitening caused by atrophy), tissue characteristics (such as the thickness, depth, or density of blood vessels, or a combination thereof), structural characteristics (such as pit pattern), or the like.

The feature region recognized by the feature region recognition unit 41 is a region including, for example, a lesion portion such as a cancer, a benign tumor portion, an inflammation portion (including, in addition to so-called inflammations, a portion with a change such as bleeding or atrophy), an ablation mark by heating, a marking portion marked by coloring with a coloring agent, a fluorescent agent, or the like, or a biopsy-performing portion subjected to a biopsy. That is, a region including a lesion, a region of a potential lesion, a region subjected to some treatment such as a biopsy, a treatment tool such as a clip or forceps, a region requiring detailed observation regardless of the possibility of a lesion, such as a dark region (a region where observation light is difficult to reach because of the back of the fold or the back of the lumen), or the like can be a region of interest. In the endoscope system 21, the feature region recognition unit 41 recognizes, as a feature region, a region including at least one of a lesion portion, a benign tumor portion, an inflammation portion, a marking portion, or a biopsy-performing portion.

Figure 4:
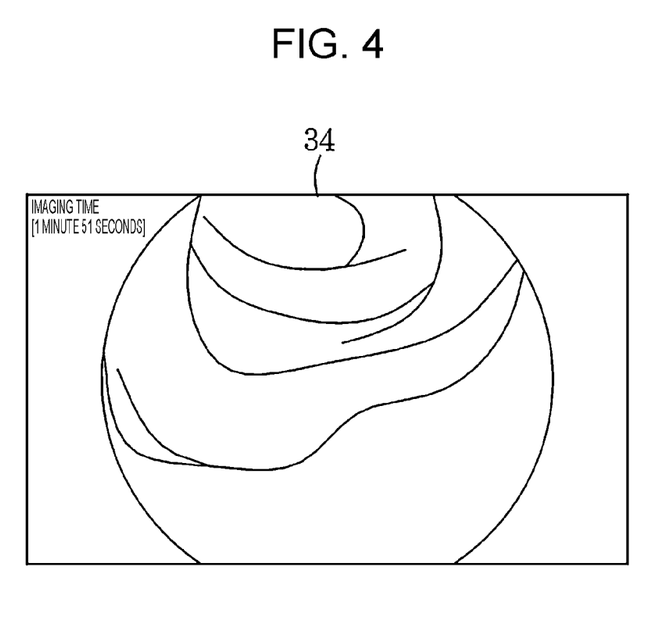
FIG. 4 is an image diagram of a medical image in which an imaging time is displayed.

The time count unit 42 count a time from a timing at which the feature region recognition unit 41 recognizes the feature region. As described below, the counted time (count time) is used to calculate a specific required time until a notification of the recognition result of the feature region is provided. In the endoscope system 21, the imaging time indicating the time that elapses from the start of imaging of the observation target is displayed. Thus, it is preferable that the time count unit 42 count the time using the imaging time. For example, as illustrated in FIG. 4, when the feature region is recognized at the point in time when the imaging time is "1 minute 50 seconds", the time count unit 42 counts "1 second" at the point in time when the imaging time becomes "1 minute 51 seconds". Thereafter, the time is counted in a similar manner. The count time is expressed in, for example, "seconds", but any other unit may be used.

In the endoscope system 21, furthermore, when the number of frames indicating the number of medical images obtained by imaging of the observation target using the endoscope 31 is counted as the number of acquired frames, it is preferable that the time count unit 42 count the time using the number of frames. For example, in a case where the frame rate is 60 FPS (Frames Per Second), if the feature region is recognized at the point in time when the number of acquired frames is "100", the time count unit 42 counts "1 second" at the point in time when the number of frames becomes "160". Thereafter, the time is counted in a similar manner.

Figure 5:
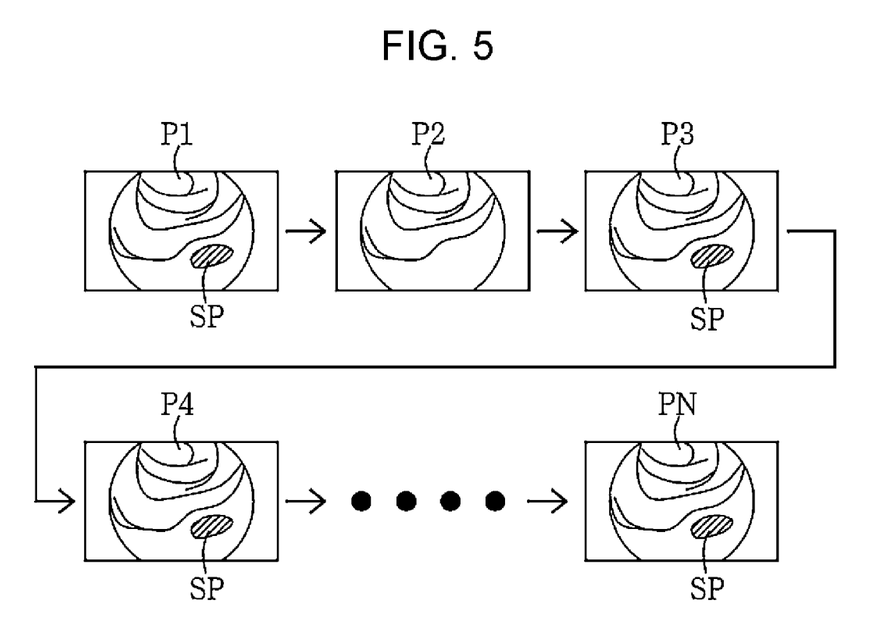
FIG. 5 is an image diagram of medical images at first to N-th timings.

As illustrated in FIG. 5, when a feature region SP is recognized in a medical image P1 at a first timing, the identical-region determination unit 43 determines whether the identical feature region is also present in a medical image PN at an N-th timing different from the first timing (N is a natural number greater than or equal to 2). For example, even when the identical feature region SP is not detected in a medical image P2 at a second timing, the identical-region determination unit 43 determines that the identical feature region is present if the identical feature region SP is detected in a medical image P3 at a subsequent third timing. If the identical-region determination unit 43 determines that the identical feature region SP is present, the time count unit 42 continues counting the count time for the identical feature region SP. On the other hand, if the identical-region determination unit 43 determines that the identical feature region SP is not present in any of the medical images P2 to PN at the second to N-th timings, the time count unit 42 resets the counted time. If the identical-region determination unit 43 determines that the identical feature region is not present, it is preferable that the time count unit 42 temporarily stop counting the time.

The remaining time calculation unit 44 calculates the remaining time until a notification of the recognition result of the feature region is provided, based on a notification waiting time and the count time counted by the time count unit 42, the notification waiting time indicating the time from when the feature region is recognized to when the notification of the recognition result of the feature region is started. Specifically, the remaining time calculation unit 44 subtracts the count time from the notification waiting time to calculate the remaining time. For example, when the notification waiting time is "5 seconds" and the count time is "1 second", the remaining time is "4 seconds" ("5 seconds"-"1 second"). The notification waiting time is preferably set in advance, and may be appropriately changeable by the user (performed by a user interface (not illustrated)).

Figure 6:
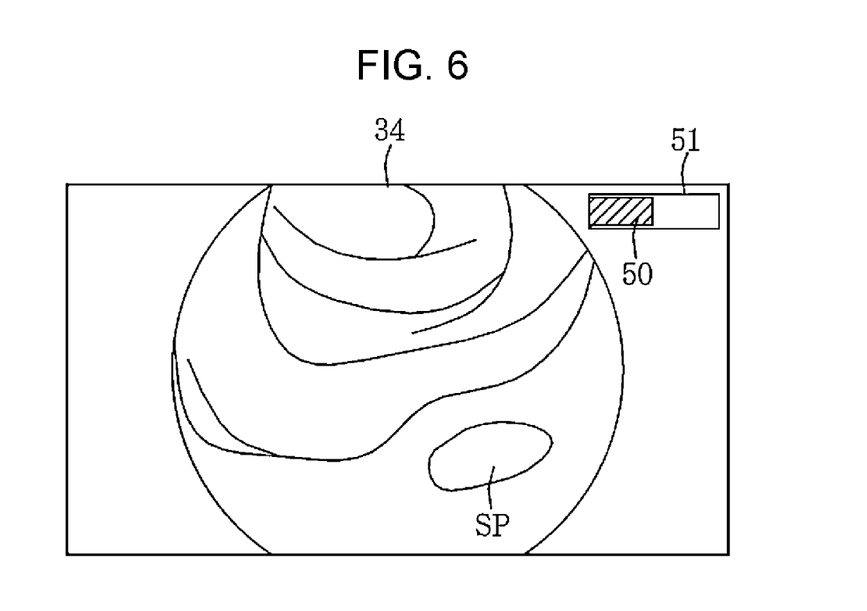
FIG. 6 is an image diagram of a medical image in which a remaining time notification time bar is displayed.
Figure 7:
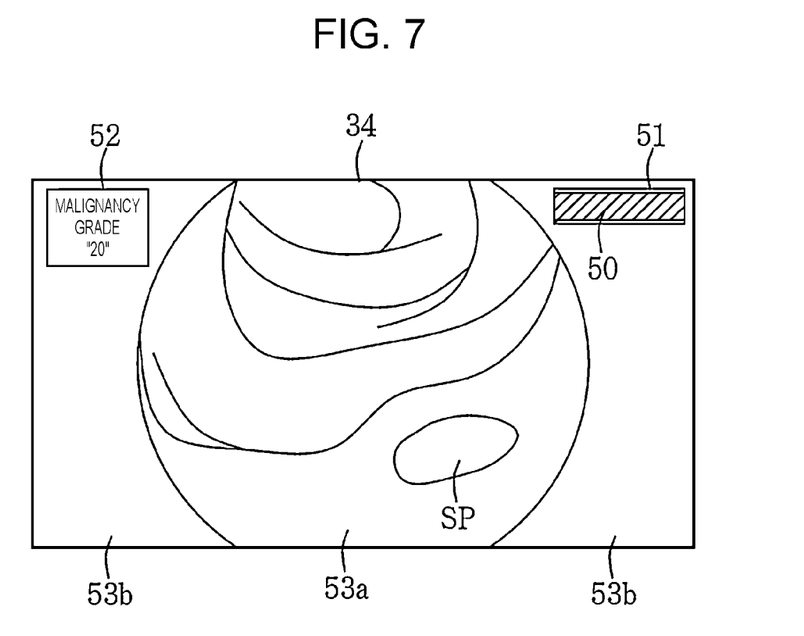
FIG. 7 is an image diagram of a medical image in which a discrimination result and the remaining time notification time bar are displayed.

The remaining time notification information generation unit 45 generates remaining time notification information for providing a notification of the remaining time, based on the remaining time calculated by the remaining time calculation unit 44. The generated remaining time notification information is displayed on the monitor 34 by the display control unit 37. As illustrated in FIG. 6, the remaining time notification information may be, for example, a remaining time notification time bar 50 indicating the remaining time. The length of the remaining time notification time bar 50 increases as the remaining time decreases. The length refers to the horizontal length of the bar. It is preferable that a notification-waiting-time time bar 51 indicating the notification waiting time be displayed at a position corresponding to the remaining time notification time bar 50. When the length of the remaining time notification time bar 50 increases with the count time and the length of the remaining time notification time bar 50 matches the length of the notification-waiting-time time bar 51, as illustrated in FIG. 7, a discrimination result 52 (malignancy grade "20") is displayed on the monitor 34 as the recognition result of the feature region SP. While the discrimination result 52 is displayed in an outer screen 53b different from an inner screen 53a where an image indicating the observation target is displayed, the discrimination result 52 may be displayed in the inner screen 53a.

The remaining time notification time bar 50 and the notification-waiting-time time bar 51 may be displayed such that length of the remaining time notification time bar 50 and the length of the notification-waiting-time time bar 51 are the same at the point in time when the feature region is recognized, with the length of the remaining time notification time bar 50 decreasing as the remaining time decreases. The remaining time or the notification waiting time may be represented by a bar, or the remaining time or the notification waiting time may be represented by any other remaining time notification geometric shape or notification-waiting-time geometric shape such as a circle.

As described above, when the user is caused to wait during the notification waiting time without being notified of the recognition result, the remaining time notification time bar 50 is used to provide a notification of the remaining time until the notification of the recognition result. This allows the user to grasp that the feature region recognition processing is being performed correctly without failure. After the notification of the recognition result, the diagnosis result by the user and the recognition result are compared and examined, thereby improving diagnosis accuracy.

Figure 8:
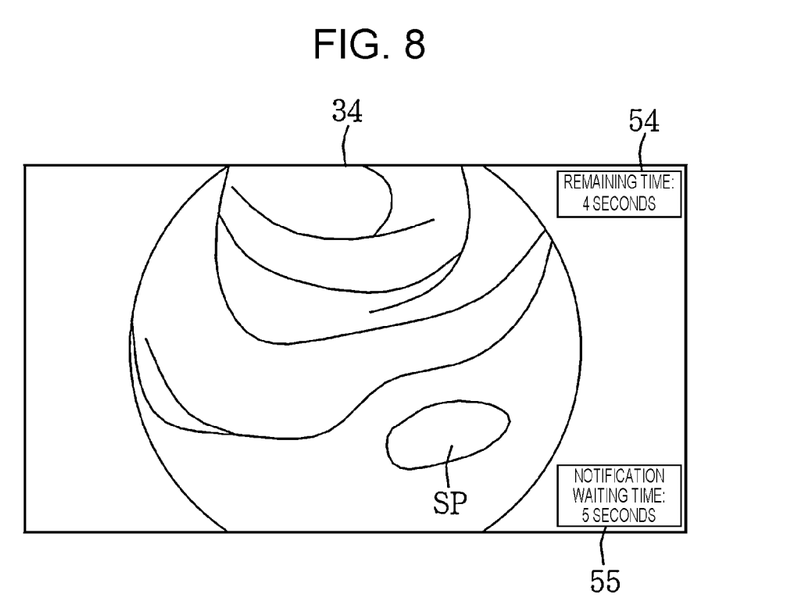
FIG. 8 is an image diagram of a medical image in which a remaining time notification value is displayed.
Figure 9:
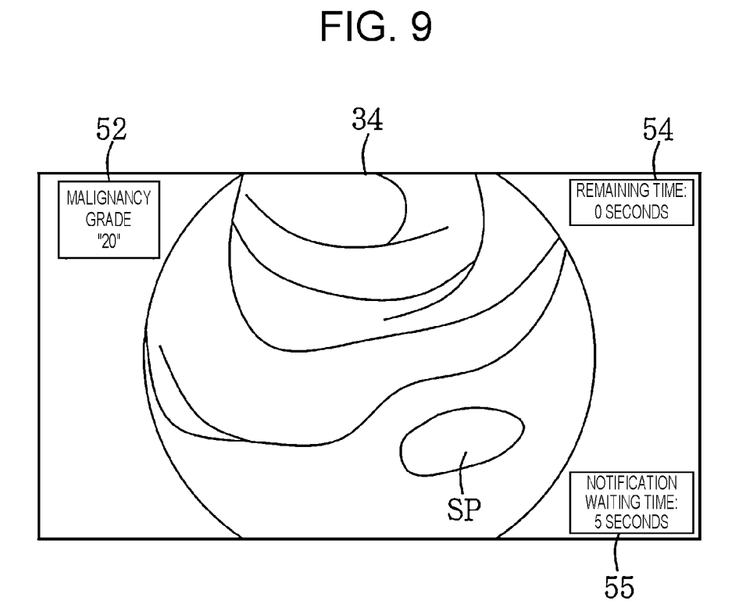
FIG. 9 is an image diagram of a medical image in which the discrimination result and the remaining time notification value are displayed.

Alternatively, as illustrated in FIG. 8, the remaining time notification information may be, for example, a remaining time notification value indicating the remaining time. The remaining time notification value is a value indicating the remaining time. For example, when the remaining time is "4 seconds", a remaining time notification value 54 representing "4 seconds" is displayed on the monitor 34. In this case, it is preferable to also display a notification waiting time 55 (for example, "5 seconds") on the monitor 34. When the remaining time becomes "0 seconds" (when the count time reaches the notification waiting time), as illustrated in FIG. 9, the discrimination result 52 is displayed on the monitor 34 as the recognition result of the feature region SP. When the remaining time notification value is to be displayed, the color or font of the remaining time notification value may be changed according to the remaining time, or the remaining time notification value may be blinked. When the remaining time notification value is to be blinked, it is preferable to change the blinking interval according to the remaining time.

Figure 10:
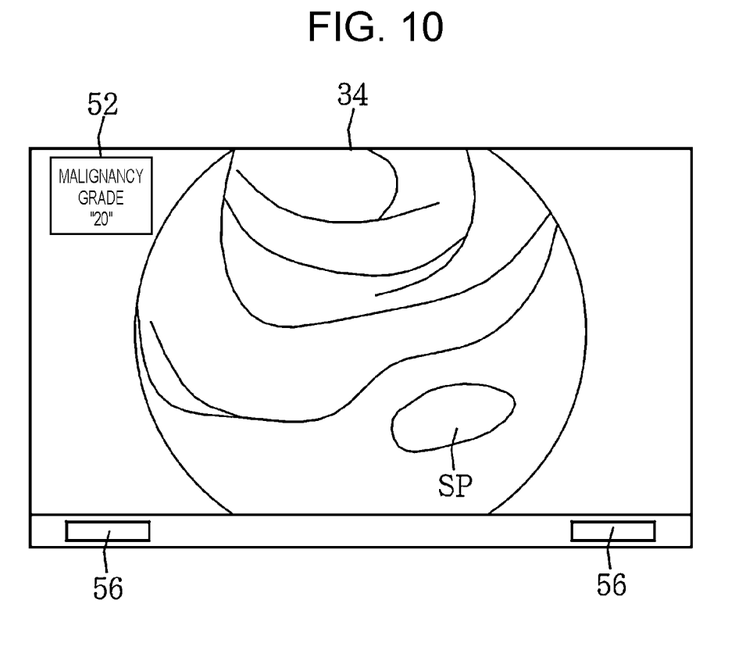
FIG. 10 is a plan view illustrating a monitor having speakers.

Alternatively, the remaining time notification information may be remaining time notification audio indicating the remaining time. The remaining time notification audio is preferably is audio including, for example, audio providing a notification of the remaining time itself. For example, the audio is preferable an audio message indicating that "it takes "4 seconds" until the notification of the recognition result is started". When the remaining time notification audio is a mechanical sound such as a beep, it is preferable that the interval over which sound is emitted be long when the remaining time is long and that the interval over which sound is emitted decrease as the remaining time decreases. When the remaining time notification audio notifies that the remaining time becomes "0 seconds" (when the count time reaches the notification waiting time), the discrimination result 52 is displayed on the monitor 34 as the recognition result of the feature region SP. As illustrated in FIG. 10, for example, the remaining time notification audio is preferably emitted from speakers 56 below the monitor 34.

Figure 11:
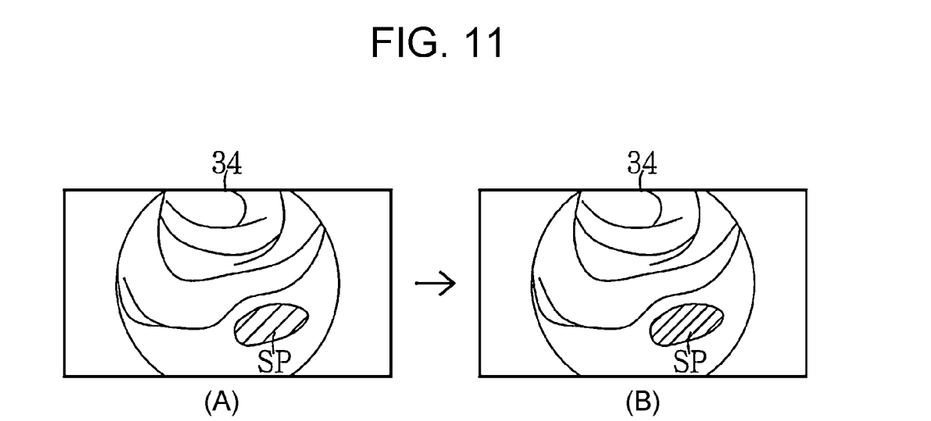
FIG. 11 includes explanatory diagrams illustrating notification of the remaining time using the level of highlighting applied to the feature region, in which part (A) is an explanatory diagram illustrating a low level of highlighting and part (B) is an explanatory diagram illustrating a high level of highlighting.
Figure 12:
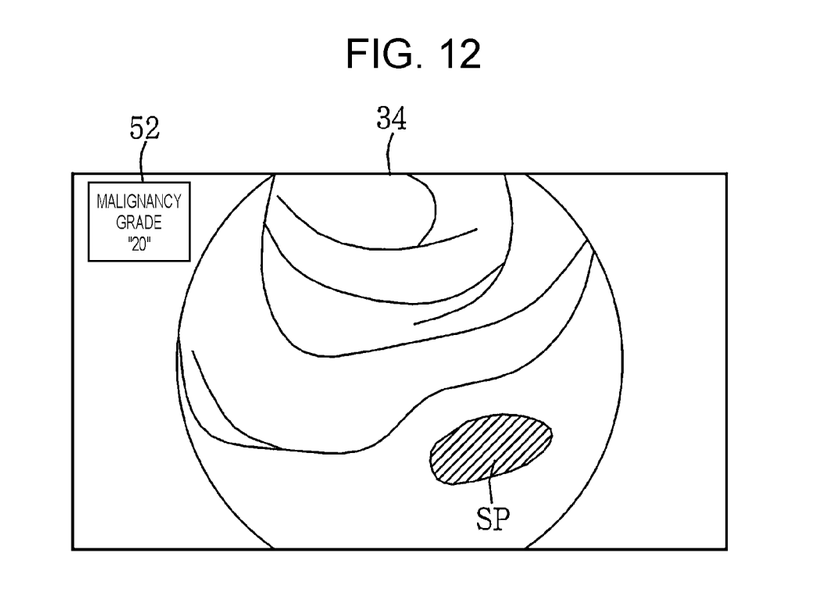
FIG. 12 is an image diagram of a medical image in which a highlighted feature region and the discrimination result are displayed.

Further, the remaining time notification information is preferably a display style of the recognition result of the feature region on the monitor 34 that changes in accordance with the remaining time. The display style of the recognition result is preferably highlighting to be applied to the feature region, such as in pseudo-color. For example, as illustrated in part (A) of FIG. 11, when the remaining time is long (in part (A) of FIG. 11, "4 seconds"), the level of highlighting for the feature region SP is reduced to notify that the remaining time is still sufficient. The highlighting level is represented by the scale of hatching such that the highlighting level increases as the scale of hatching is finer. As illustrated in part (B) of FIG. 11, as the remaining time deceases (in part (B) of FIG. 11, "1 second"), the level of highlighting for the feature region SP increases, thereby notifying that the remaining time is short and the recognition result of the feature region is presented soon. When the remaining time becomes "0 seconds" (when the count time reaches the notification waiting time), as illustrated in FIG. 12, the highlighting level for the feature region SP is maximized, and the discrimination result 52 is displayed on the monitor 34 as the recognition result of the feature region SP. As described above, changing the display style of the feature region to provide a notification of the remaining time. This allows the user to grasp the remaining time without shifting the line of sight from the feature region.

Figure 13:
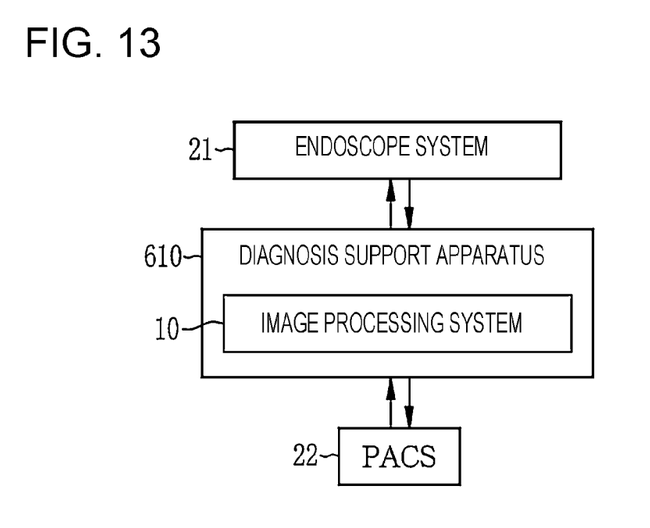
FIG. 13 illustrates a diagnosis support apparatus including the image processing system.
Figure 14:
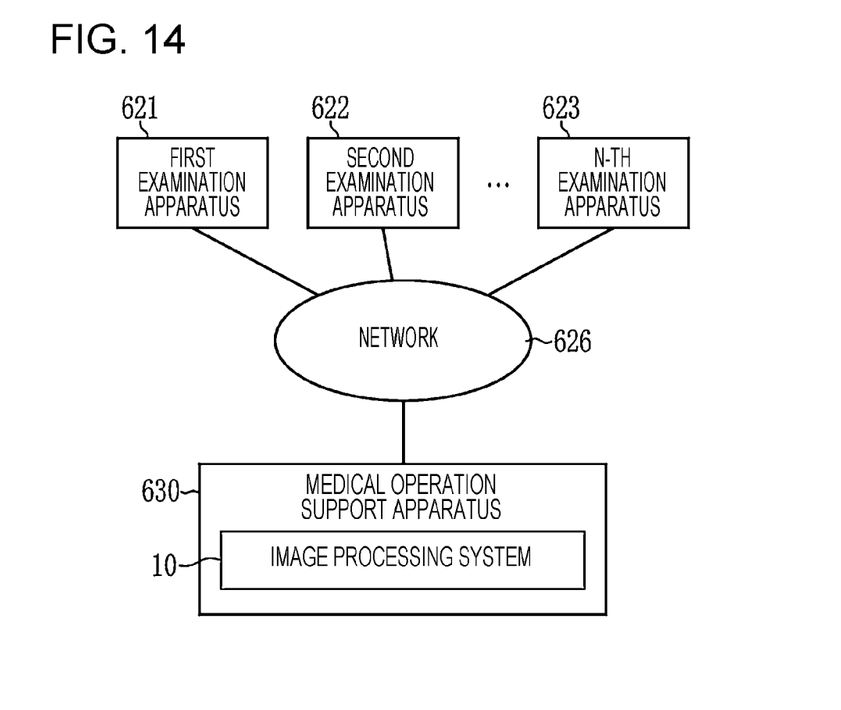
FIG. 14 illustrates a medical operation support apparatus including the image processing system.

As illustrated in FIG. 13, a diagnosis support apparatus 610 to be used in combination with the endoscope system 21 or any other modality and the PACS 22 can include the image processing system 10 according to the embodiment described above and other modifications. As illustrated in FIG. 14, for example, a medical operation support apparatus 630 including the endoscope system 21 and to be connected to various examination apparatuses such as a first examination apparatus 621, a second examination apparatus 622, . . . , and an N-th examination apparatus 623 via a desired network 626 can include the image processing system 10 according to the embodiment described above and other modifications.

Additionally, the image processing system 10, the endoscope system 21, and various apparatuses or systems including the image processing system 10 can be used with various modifications or the like described below.

As the medical image, a normal light image obtained by irradiation with light in the white range or, as light in the white range, light in a plurality of wavelength ranges.

When an image obtained by irradiation with light in a specific wavelength range is used as the medical image, the specific wavelength range may be a range narrower than the white wavelength range.

The specific wavelength range is, for example, the blue range or green range in the visible range.

When the specific wavelength range is the blue range or green range in the visible range, preferably, the specific wavelength range includes a wavelength range greater than or equal to 390 nm and less than or equal to 450 nm or greater than or equal to 530 nm and less than or equal to 550 nm, and light in the specific wavelength range has a peak wavelength in a wavelength range greater than or equal to 390 nm and less than or equal to 450 nm or greater than or equal to 530 nm and less than or equal to 550 nm.

The specific wavelength range is, for example, the red range in the visible range.

When the specific wavelength range is the red range in the visible range, preferably, the specific wavelength range includes a wavelength range greater than or equal to 585 nm and less than or equal to 615 nm or greater than or equal to 610 nm and less than or equal to 730 nm, and light in the specific wavelength range has a peak wavelength in a wavelength range greater than or equal to 585 nm and less than or equal to 615 nm or greater than or equal to 610 nm and less than or equal to 730 nm.

The specific wavelength range may include, for example, a wavelength range in which a light absorption coefficient is different between oxyhemoglobin and reduced hemoglobin, and light in the specific wavelength range may have a peak wavelength in a wavelength range in which a light absorption coefficient is different between oxyhemoglobin and reduced hemoglobin.

When the specific wavelength range includes a wavelength range in which a light absorption coefficient is different between oxyhemoglobin and reduced hemoglobin, and light in the specific wavelength range has a peak wavelength in a wavelength range in which a light absorption coefficient is different between oxyhemoglobin and reduced hemoglobin, preferably, the specific wavelength range includes a wavelength range of 400±10 nm, 440±10 nm, 470±10 nm, or greater than or equal to 600 nm and less than or equal to 750 nm, and light in the specific wavelength range has a peak wavelength in a wavelength range of 400±10 nm, 440±10 nm, 470±10 nm, or greater than or equal to 600 nm and less than or equal to 750 nm.

When the medical image is an in-vivo image obtained by imaging of the inside of a living body, the in-vivo image may have information on fluorescence emitted from a fluorescent substance in the living body.

As the fluorescence, fluorescence obtained by irradiation of the inside of a living body with excitation light having a peak wavelength greater than or equal to 390 nm and less than or equal to 470 nm may be used.

When the medical image is an in-vivo image obtained by imaging of the inside of a living body, the wavelength range of infrared light may be used as the specific wavelength range described above.

When the medical image is an in-vivo image obtained by imaging of the inside of a living body and the wavelength range of infrared light is used as the specific wavelength range described above, preferably, the specific wavelength range includes a wavelength range greater than or equal to 790 nm and less than or equal to 820 nm or greater than or equal to 905 nm and less than or equal to 970 nm, and light in the specific wavelength range has a peak wavelength in a wavelength range greater than or equal to 790 nm and less than or equal to 820 nm or greater than or equal to 905 nm and less than or equal to 970 nm.

The medical image acquisition unit 11 can have a special light image acquisition unit that acquires a special light image having a signal in the specific wavelength range on the basis of a normal light image obtained by irradiation with light in the white range or, as light in the white range, light in a plurality of wavelength ranges. In this case, the special light image can be used as the medical image.

The signal in the specific wavelength range can be obtained by calculation based on color information of RGB or CMY included in the normal light image.

A feature value image generation unit can be included that generates a feature value image by using calculation based on at least one of a normal light image obtained by irradiation with light in the white range or, as light in the white range, light in a plurality of wavelength ranges and a special light image obtained by irradiation with light in the specific wavelength range. In this case, the feature value image can be used as the medical image.

In the endoscope system 21, a capsule endoscope can be used as the endoscope 31. In this case, the light source device 32 and a portion of the processor device 33 can be mounted in the capsule endoscope.

In the embodiment described above and modifications, the hardware structure of processing units that execute various types of processing, such as the medical image acquisition unit 11, the medical image analysis processing unit 12, the display control unit 15, the input receiving unit 16, the overall control unit 17, the medical image acquisition unit 35, the medical image analysis processing unit 36, the display control unit 37, the feature region recognition unit 41, the time count unit 42, the identical-region determination unit 43, the remaining time calculation unit 44, and the remaining time notification information generation unit 45, is implemented as various processors described hereinbelow. The various processors include a CPU (Central Processing Unit), which is a general-purpose processor executing software (program) to function as various processing units, a programmable logic device (PLD) such as an FPGA (Field Programmable Gate Array), which is a processor whose circuit configuration is changeable after manufacture, a dedicated electric circuit, which is a processor having a circuit configuration specifically designed to execute various types of processing, a GPU (Graphical Processing Unit), and so on.

A single processing unit may be configured as one of the various processors or as a combination of two or more processors of the same type or different types (for example, a plurality of FPGAs, a combination of a CPU and an FPGA, or a combination of a CPU and a GPU). Alternatively, a plurality of processing units may be configured as a single processor. Examples of configuring a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various processing units are configured by using one or more of the various processors described above as a hardware structure.

More specifically, the hardware structure of these various processors is an electric circuit (circuitry) in which circuit elements such as semiconductor elements are combined. The hardware structure of the storage unit is a storage device such as an HDD (hard disc drive) or an SSD (solid state drive).

Another embodiment of the present invention is as follows.

A medical image processing system of the present invention includes a processor device configured to, acquire, using a medical image acquisition unit, a medical image obtained by imaging of an observation target, recognize, using a feature region recognition unit, a feature region in the medical image, count, using a time count unit, a time from a timing at which the feature region is recognized, calculate, using a remaining time calculation unit, a remaining time until a notification of a recognition result of the feature region is provided, based on a notification waiting time and a count time counted by the time count unit, the notification waiting time indicating a time from when the feature region is recognized to when the notification of the recognition result of the feature region is started, and display, using a display control unit, remaining time notification information on a display unit, the remaining time notification information being obtained based on at least the remaining time.

REFERENCE SIGNS LIST

10 image processing system
11 medical image acquisition unit
12 medical image analysis processing unit
13 display unit
15 display control unit
16 input receiving unit
17 overall control unit
18 storage unit
21 endoscope system
22 PAC S
31 endoscope
32 light source device
33 processor device
34 monitor
35 medical image acquisition unit
36 medical image analysis processing unit
37 display control unit
41 feature region recognition unit
42 time count unit
43 identical-region determination unit
44 remaining time calculation unit
45 remaining time notification information generation unit
50 remaining time notification time bar
51 notification-waiting-time time bar
52 discrimination result
53$a$ inner screen
53$b$ outer screen
54 remaining time notification value
55 notification waiting time
56 speaker
610 diagnosis support apparatus
621 first examination apparatus
622 second examination apparatus
N-th examination apparatus
626 network
630 medical operation support apparatus
SP feature region
P1 medical image at first timing
P2 medical image at second timing
P3 medical image at third timing
P4 medical image at fourth timing
PN medical image at N-th timing

What is claimed is:

1. A medical image processing system comprising:
a processor configured to function as:
a medical image acquisition unit that acquires a medical image obtained by imaging of an observation target;
a feature region recognition unit that recognizes a feature region in the medical image;
a time count unit that counts a time from a timing at which the feature region is recognized;
a remaining time calculation unit that calculates a remaining time until a notification of a recognition result of the feature region is provided, based on a notification waiting time and a count time counted by the time count unit, the notification waiting time indicating a time from when the feature region is recognized to when the notification of the recognition result of the feature region is started; and
a display control unit that displays remaining time notification information on a display at a point in time when the feature region is recognized, the remaining time notification information being obtained based on at least the remaining time.

2. The medical image processing system according to claim 1, wherein the remaining time notification information is represented by a remaining time notification geometric shape representing the remaining time using a geometric shape, and the remaining time notification geometric shape changes to notify the remaining time in accordance with the remaining time.

3. The medical image processing system according to claim 2, wherein the remaining time notification geometric shape is a time bar.

4. The medical image processing system according to claim 1, wherein the remaining time notification information is a remaining time notification value representing the remaining time using a value.

5. The medical image processing system according to claim 1, wherein the remaining time notification information is remaining time notification audio representing the remaining time using audio.

6. The medical image processing system according to claim 1, wherein the remaining time notification information is a display style of the recognition result of the feature region that changes in accordance with the remaining time.

7. The medical image processing system according to claim 6, wherein the display style of the recognition result is highlighting applied to the feature region.

8. The medical image processing system according to claim 1, wherein the recognition result includes a result of discrimination processing for discriminating the feature region.

9. The medical image processing system according to claim 1, wherein the time count unit counts the time based on an imaging time related to imaging of the observation target.

10. The medical image processing system according to claim 1, wherein the time count unit counts the time based on the number of acquired frames indicating the number of medical images that are acquired.

11. The medical image processing system according to claim 1, wherein the processor further configured to function as:
  an identical-region determination unit that determines, in a case where the feature region is recognized in a medical image at a first timing, whether a feature region that is identical to the feature region is also present in a medical image at an N-th timing different from the first timing, and
  wherein the time count unit continues counting the time when it is determined that the identical feature region is present.

12. The medical image processing system according to claim 1, wherein the display control unit displays the recognition result of the feature region on the display in response to the count time reaching the notification waiting time.

* * * * *